(12) United States Patent
Smolko et al.

(10) Patent No.: US 6,284,117 B1
(45) Date of Patent: Sep. 4, 2001

(54) APPARATUS AND METHOD FOR REMOVING SMALL MOLECULES AND IONS FROM LOW VOLUME BIOLOGICAL SAMPLES

(75) Inventors: Daniel Smolko, Jamul; Ed Sheldon, San Diego; Paul Swanson, Santee; Prashant P. Mehta, Carlsbad; Manuel Jimenez, San Diego; Kenneth A Bloch, S.D.; Lorelei Westin, La Mesa; Geoffrey C. Landis, Carlsbad, all of CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/469,588

(22) Filed: Dec. 22, 1999

(51) Int. Cl.[7] .................................................. B01D 61/44
(52) U.S. Cl. ..................... 204/543; 204/640; 210/638; 210/645; 210/321.87; 210/321.89
(58) Field of Search ................... 204/543, 640; 210/321.87, 321.89, 638, 645

(56) References Cited

U.S. PATENT DOCUMENTS

| | | | |
|---|---|---|---|
| 4,632,745 | 12/1986 | Giuffrida et al. | 204/301 |
| 5,026,465 | 6/1991 | Katz et al. | 204/182.4 |
| 5,316,637 | 5/1994 | Ganzi et al. | 204/182.4 |
| 5,593,563 | 1/1997 | Denoncourt et al. | 204/524 |
| 5,632,957 | 5/1997 | Heller et al. | 422/68.1 |

OTHER PUBLICATIONS

Spiegler, *Salt Water Purification*, 2nd ed., Plenum Press, New York (1977), No month available, only title page, index.

*Primary Examiner*—Arun S. Phasge
(74) *Attorney, Agent, or Firm*—Lyon & Lyon LLP (57) ABSTRACT

This invention provides an apparatus and method for desalting a low volume solution for use in connection with an electronically addressable microarray. The apparatus comprises a tubular molecular weight cut-off membrane embedded within a ion exchange resin filled chamber. The apparatus provides a very high surface to volume ratio of membrane pore surface to exchange resin capacity for absorbing charged molecules. The design facilitates the speedy removal of charged molecules from test solutions with the resultant desalted solution having a very low ionic strength suitable for use in the electronic transport of nucleic acids, proteins, and cells.

18 Claims, 8 Drawing Sheets

APPARATUS AND METHOD FOR REMOVING SMALL MOLECULES AND IONS FROM LOW VOLUME BIOLOGICAL SAMPLES

GOVERNMENT SUPPORT

The Government has rights in this invention pursuant to Grant Nos. ATP I: 70NANB5H1107 and ATP II: 70NANB7H3001 awarded by the Advanced Technology Program.

FIELD OF THE INVENTION

This invention relates generally to the lowering of small and charged molecule concentration from a solution. More particularly, this invention relates to the lowering of ion concentration and relatively small molecules from solutions containing biological materials such as nucleic acids, proteins, and cells. Even more specifically, this invention relates to the lowering of ion concentration and removing oligonucleotide primer molecules in samples containing biological materials such as amplified nucleic acids in very small volumes such as used in microarray assay environments.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

There has been much work in the field of desalting solutions in macroscopic environments. For example, devices and methods have been developed for removal of charged particles, such as ions, using various forms of chromatography including dialysis across permeable membranes, ion exchange resins, size exclusion resins, and electrodialysis and the like. Typically, these macroscale devices and methods have involved the use of passive removal or exchange of materials by diffusion. These systems require, generally, large volumes of fluids to accomplish the desired ion removal or exchange and achieve the desired ionic strength.

For example, desalting using permeable membranes generally involves use of dialysis tubing having a pore size cut-off that allows various sized materials to pass through the membrane. Such processes might also use a planar membrane whereby a solution to be desalted is passed next to said membrane and ions are exchanged by diffusion. In such systems, the solution is re-circulated for an extended period of time until the ionic strength of the solution is reduced.

In another example, ion exchange resins are typically employed to desalt a solution wherein the solution is passed directly over the exchange resin, such as in a column. Like dialysis, this requires copious amounts of solution volume. Additionally, such a means of desalting presents very large surface area over which a sample, with its target materials, must pass thereby allowing valuable target materials to be lost from the sample by nonspecific binding. Size exclusion resins are used in a similar fashion and present the same types of problems.

In still another example, electrodialysis has been used as applied to desalting copious volumes of water. Specifically, such systems have been used successfully to desalinate sea water wherein charged permselective membranes trap ions with like charge behind similarly charged membranes in a direct current field. (Spiegler, Salt Water Purification, $2^{nd}$ ed., Plenum Press, New Your, 1977). Systems such as this that use electronic potential have additional drawbacks in that with increasing time of electrolysis, there is an increasing drop in voltage potential across the permselective membrane due to the buildup of charge across the membrane and this causes decrease in desalinization efficiency. This efficiency problem has been addressed by employing ion exchange resins to sequester the ions once they have been transported across the membrane thereby reducing the local ion concentration. (see U.S. Pat. Nos. 5,316,637, 4,632,745, 5,593,563, and 5,026,465)

Major drawbacks to each of the above methods include the rate at which desalting can occur as well as a limitation of the degree to which desalting can occur. Generally, in such systems, desalting cannot be carried out in an economical fashion to the levels necessary for applicability to micro-volume scales, especially those systems which require use of electronic potentials applied to the micro-volume to induce transport of molecules within the volumes from one point to another. With respect to the current invention, such systems comprise electronically addressable microarrays used in the amplification, isolation, and identification of nucleic acids, proteins, and cells.

Given that there is still a need in the arts for devices and methods capable of efficiently and quickly desalting small volume samples used in connection with electronically addressable microarrays, we have solved such problems by providing a device and method capable of desalting a low volume sample generally in less than 15 minutes, usually in less than 5 minutes, and preferably in less than 3 minutes, to a level of ionic strength, generally less than 100 uS/cm, and preferably less than 50 uS/cm, wherein said sample can be applied to an electronically addressable microarray and analyzed.

SUMMARY OF THE INVENTION

Embodiments of the current invention address problems caused by high ionic strength conditions of low volume solutions containing molecules of interest. Particularly, this invention provides apparatus and methods for lowering ion concentration in such solutions to a level that will allow electronic transport of the molecules of interest without interference from free ions or other charged small molecules in the solutions. For example, it has been observed that problems with transport are encountered with nucleic acids following amplification reactions (e.g., PCR and strand displacement amplification (SDA)) wherein the reaction solutions use high ionic strength conditions. Prior to this invention ionic strength could only be lowered by diluting the reaction solution or using a desalting column either of which resulted in loss of target due to reduction in concentration, insufficient reduction of ionic strength, and further loss of time in completion of the assay.

The high ionic strength level in a sample solution inhibits electronic transport of molecules that are sensitive to an electric field, such as nucleic acids. This is because as electronic potential is applied to the solution, if ions are present, they tend to carry charge and are transported instead of the larger molecules of interest. Thus, ions will migrate to electrode pads of an electronically addressable microarray such as those designated the "APEX chip" as disclosed in U.S. Pat. No. 5,632,957 herein incorporated by reference, instead of the larger molecules of interest.

We have found that desalting microsolutions such as that used in connection with electronically addressable microarrays not only requires an efficient means by which the solution can be desalted to appropriate levels of ionic strength, but also requires an efficient and quick method and apparatus for desalting assay solutions for integration into a cartridge format for in-line desalting coupled to the microarray assay.

Thus, in one embodiment of the invention, an apparatus having elements of the invention is integrated onto the cartridge containing the microarray for in-line desalting of the assay solution prior to the solution's introduction to the microarray.

In another embodiment, the apparatus of the invention comprises a tubular molecular weight cut off membrane that generally has a molecular weight cut off no greater than 500 kDa. The invention having a pore size of this limit allows for the easy exchange of most small charged molecules and ions without allowing loss of larger proteins, nucleic acids, and cells of interest. Generally, it is contemplated that the cut off will allow ions to pass but not larger molecules. In other embodiments, the cut off may be set to allow small nucleic acid molecules such as oligo primers to pass.

In a further embodiment, the apparatus comprises lumen diameters of the tubular membrane that are useful in the transport of various sized structures such as molecules versus whole cells.

In a further embodiment, the apparatus may comprise more than one tubular membrane positioned in parallel to one another for processing different samples simultaneously. Where at least one tubular membrane is contemplated, it is contemplated that samples may also be processed in series.

In a further embodiment, the apparatus contemplates embedding the tubular membrane within a bed of mixed cation and/or anion exchange resin that is enclosed within a nonpermeable housing such as a plastic tube or structure of the microarray cartridge. In this embodiment, the resin is further contemplated to comprise resins of various sizes such as granulated and/or fine powders. The choice of which type resin to use in any particular application will vary depending upon the nature of the solution and content of target molecular structures of the solution being desalted. It is contemplated that varying the granulation of the resins will affect the time required for the solution to become desalted to appropriate levels for use of the desalted solution in the electronically addressable microarray.

In another embodiment, the invention contemplates that a low ionic strength buffer be used to wet and optionally circulate through the resin bed, which has been previously saturated with the same concentration of buffer. This aids the deionization of the sample by introducing a low conductivity assay buffer directly into the sample solution within the tubular membrane and consequently helps reduce the time required for desalting of the solution.

In still further embodiments, it is contemplated that the apparatus and method use electrodes capable of measuring the ionic strength of the solution to be desalted and that such electrodes be optionally placed in the tubular membrane. The location where such electrodes are placed within the lumen of the tubular membrane is not particularly important but preferably they are place at or near the terminus of the tube where desalted solution exits the tube.

Still further embodiments contemplate optionally including within the resin bed electrodes for use in electodeionization and electrodialysis. In this embodiment the electrodes provide the ability to enhance desalting by application of either direct or alternating current to the solution to be desalted. Such enhancement is contemplated to comprise reducing both time for desalting as well as level of ionic strength.

DETAILED DESCRIPTION OF THE PREFERRED EMBODIMENTS

Referring now to the apparatus of the invention, in a preferred embodiment the apparatus is contemplated to comprise a tubular molecular weight cut off membrane centrally embedded within a mixed ion exchange resin bed chamber. The apparatus may comprise a single tubular membrane or more than one tubular membrane in which case the membranes are connected in parallel with respect to one another.

Additionally, the tubular membrane(s) may be positioned within the resin bed in any number of conformations including linear, coiled, and hypercoiled. By hypercoiled is meant that the tube is coiled upon itself such that one layer of coil is within another such that the coils are separated by resin. The purpose of using coils is to decrease the size of the apparatus.

Sensor electrodes may optionally be included in the membrane lumen for measuring the ionic strength of the solution as it is desalted. In a preferred embodiment, the sensor is placed near the terminus of the tube as the solution exits the apparatus.

In a further embodiment the diameter of the tubular membrane may vary depending upon the intended application of the assay to be performed. Where nucleic acids and/or proteins are to be assayed, the membrane has a lumen diameter of between 100 μm and 1 mm. Where larger structures are to be assayed, such as whole cells, the diameter may be between 500 μm and 3 mm. Whatever the diameter, the design of the apparatus provides a high diffusional surface area to volume ratio. The tube is contemplated to hold microliter (on the order of 1 to 1000 microliters) volumes of sample containing solution and providing a flow path for sample irrespective of electrode/resin/chamber geometries. The flow path is contemplated to be between 1 and 500 mm in length. Additionally, the resin bed volume can be any size but generally between 0.05 μl to 10 ml.

In a further embodiment, the molecular weight cut off is contemplated to be anywhere from 1 to 500 kDa. The membrane itself may be made of any appropriate material for free transport of proteins, nucleic acids, and whole cells including regenerated cellulose (RC), polyethersulfone (PES), polysulfone (PS), and polyvinyldifluoride (PVDF).

The resin and chamber in which the membrane is embedded is contemplated to comprise a mixed bed such that the bed have any or all of the following qualities: mixed size from granular to powder, single ion exchange resin either anion exchange or cation exchange, mixed ion exchange both cationic and anionic in nature, or buffer components including histidine, β-alanine, Tris (hydroxymethyl) aminomethane (TRIS), boric acid acetic acid and ethylenediaminetetraacetic acid (EDTA), and ports for flow through of buffer to and from the chamber.

Additionally, the resin chamber may optionally include electrodes for applying either a direct or an alternating current across the tubular membrane for the purpose of carrying out electrodeionization or electrodialysis. The electrode and mixed bed regions are wetted with water and sample which is to be desalted is introduced into the lumen of the tubular membrane. Depending upon the geometry of the apparatus, an alternating current of between 0.1 mA/cm$^2$ to 5 mA/cm$^2$, or a voltage of 2 to 100 V/cm is applied at a specified frequency of between 0.01 to 0.01 Hz. Application of such voltages and currents allows for the electrophoresis of small charged ions (ionophoresis) such as sodium ions, chloride ions, and the electrophoresis of larger molecules such as histidine ions, peptides and DNA oligos which contaminate and add to the solution conductivity. The resulting movement of these ions and subsequent sequestration in the ion exchange matrix allows desalting to occur such that conductivities as low as 10 to 22 μS/cm may be achieved within 3 minutes from samples having starting conductivities as high as 20,000 μS/cm.

The apparatus so described may be integrated into a system for performing assays on an electronically addressable microarray. In one embodiment, the apparatus of the invention is connected directly to and integrated with a cartridge containing the microarray. In this design, microchannels for passing desalted solution out of the apparatus connect the desalting apparatus to the microarray while like channels connect entrance ports of the apparatus to access ports at the edge of the cartridge. In another design, the apparatus is free standing in that it is not integrated with the cartridge but is instead placed in-line with assay units designed for carrying out sample preparation, such as nucleic acid amplification, and equipped at its terminus with ports adapted for channeling desalted solutions to the microarray.

With respect to the method of the invention, the apparatus described herein may be used to lower the ionic strength of a solution over one thousand fold in 15 minutes or less. For example, a solution comprising an SDA reaction mixture can be lowered in conductivity from a starting value of 10–20 mS/cm (10,000–20,000 uS/cm) to about 20 uS/cm in less than 15 minutes. A method of this capacity for lowering ionic strength provides ranges of conductivity that are optimal for use in assays that require the use of electronically addressable microarrays. For example, conductivity of a solution for use on such a microarray should be less than 200 uS/cm in order to realize transport of nucleic acid under typical electronic potential. It has been found that reduction of conductivity in this manner has allowed transport and recovery of 85 to 90% of a nucleic acid in an assay sample.

Described below are examples of methods of using said apparatus wherein both passive and electrodeionization are described.

EXAMPLE 1

Figure 1:
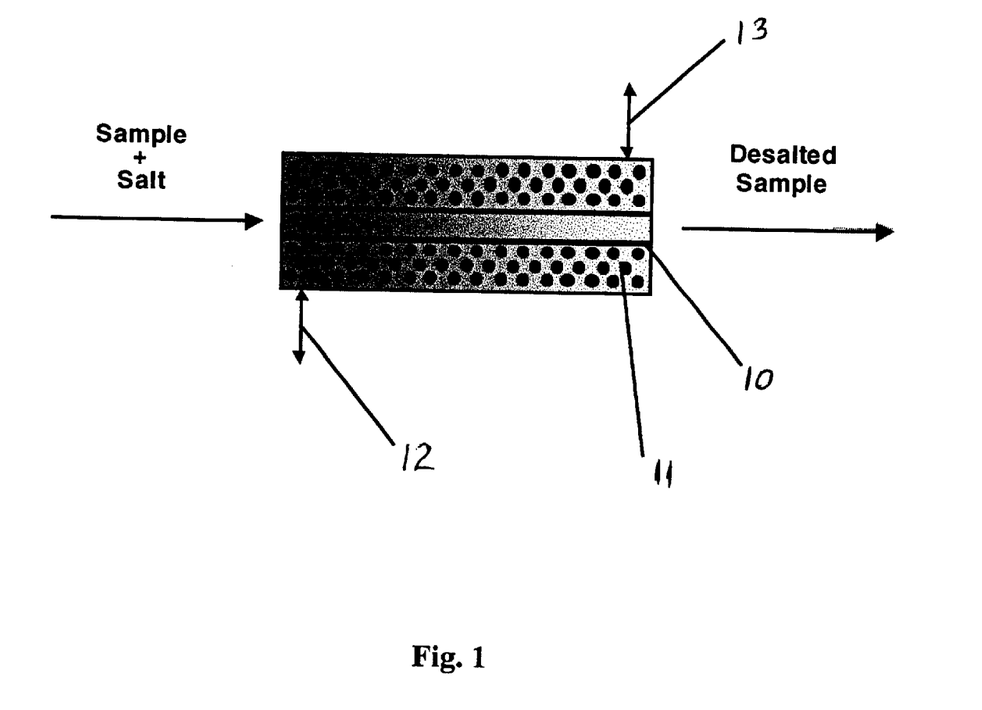
FIG. 1 is a diagram of one embodiment of the invention wherein the tubular membrane 10 has a linear design. The shell side of the device, external to the membrane lumen, contains ion exchange resin 11 encased in a chamber that optionally has ports 12 and 13 for channeling low ionic strength buffer or water.
Figure 2:
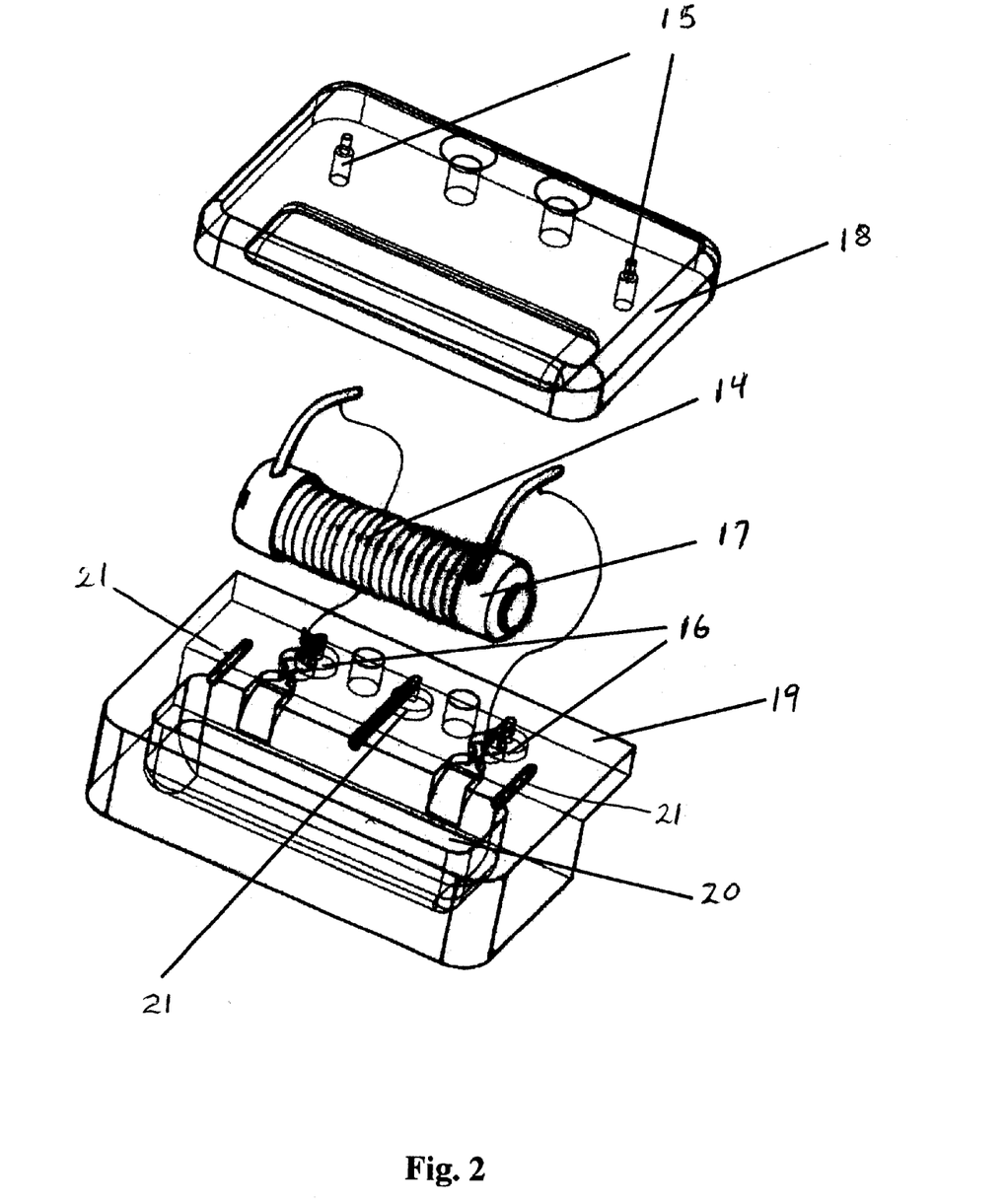
FIG. 2 is a diagram of one embodiment of the invention wherein the tubular membrane 14 is coiled such that a greater surface area of solution to be desalted per volume of resin is realized. In this design the coil is wrapped around a support 17 and is encased in housing made of two halves 18 and 19. The coil rests within chamber 20 which further has inlet and outlet ports 21 for directing fluids. The ends of the coiled tube 14 are connected to inlet and outlet ports 15 via channels 16.
Figure 3:
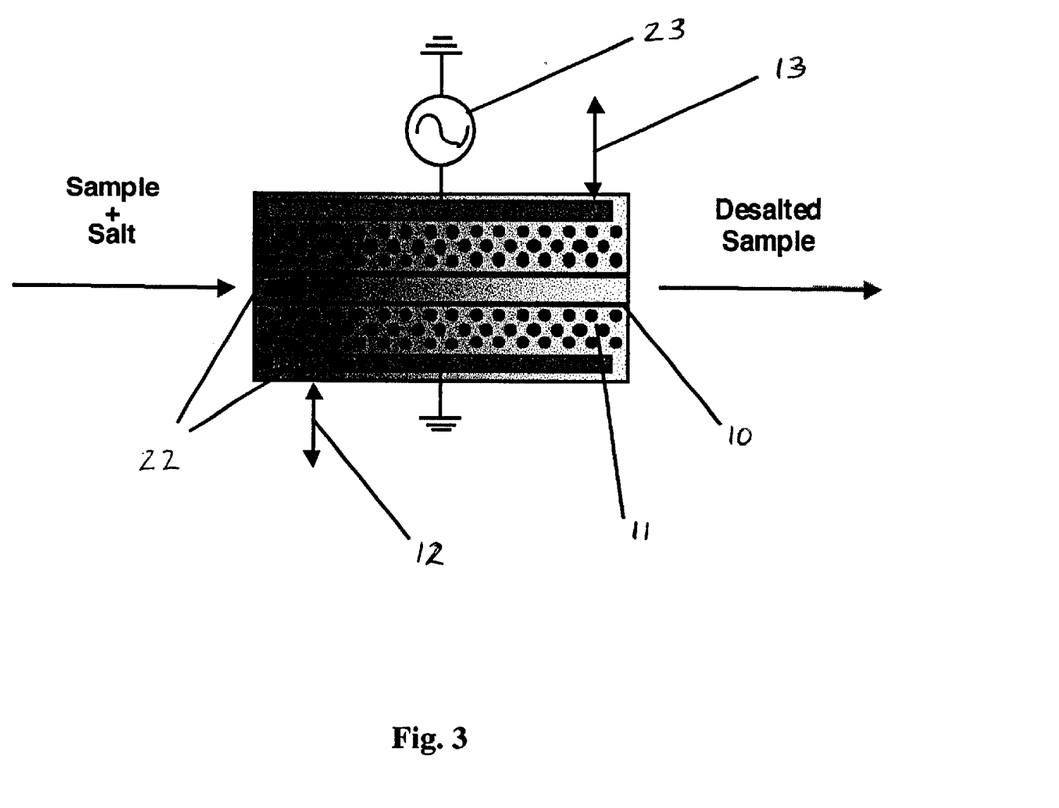
FIG. 3 is a diagram wherein there is located within the resin chamber electrodes 22 for creating an electric potential, DC or an oscillating waveform, by external source 23 so that the solution to be desalted can be electrically deionized in addition to a passive deionization. As with the embodiment displayed in FIG. 2, the tubular membrane can be coiled.
Figure 4:
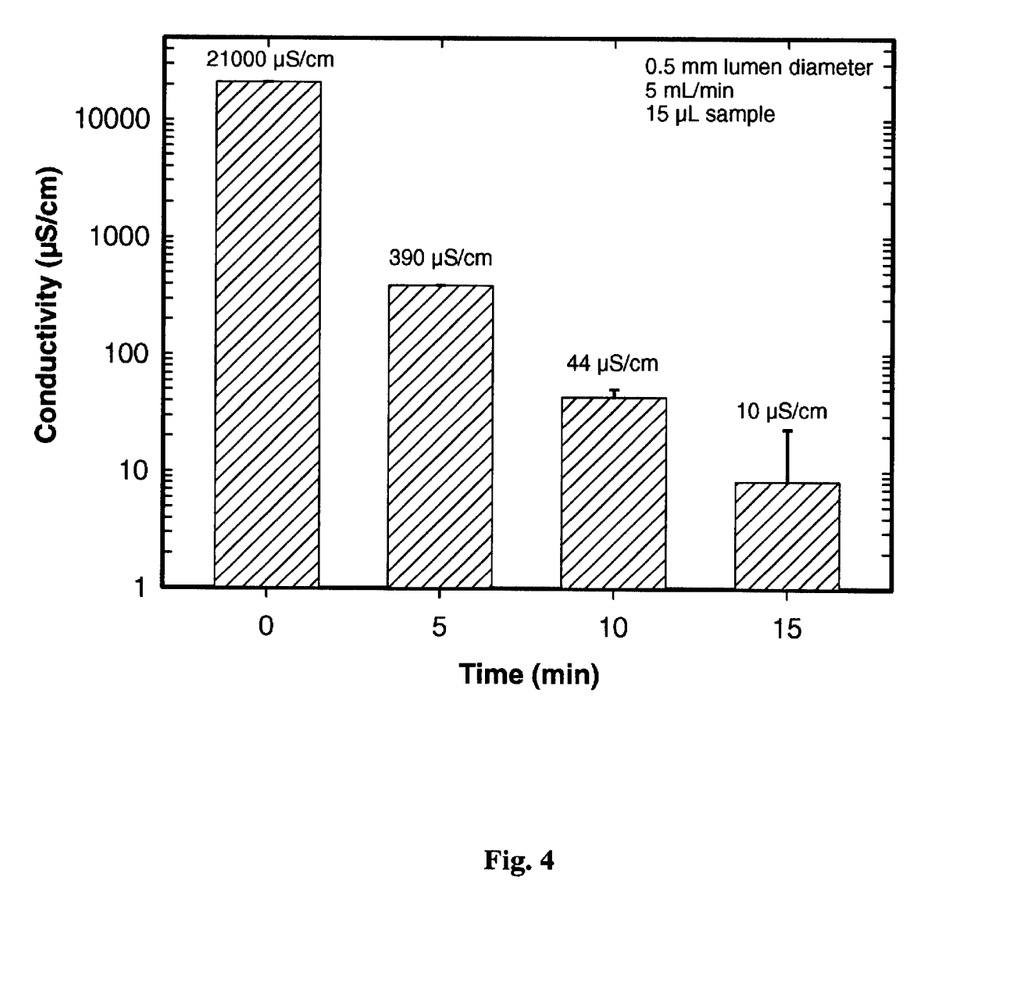
FIG. 4 is a bar chart showing reduction in conductivity of a test solution versus time. The values for 5, 10, and 15 minutes are 390, 44, and 10 $\mu$S/cm respectively.
Figure 5:
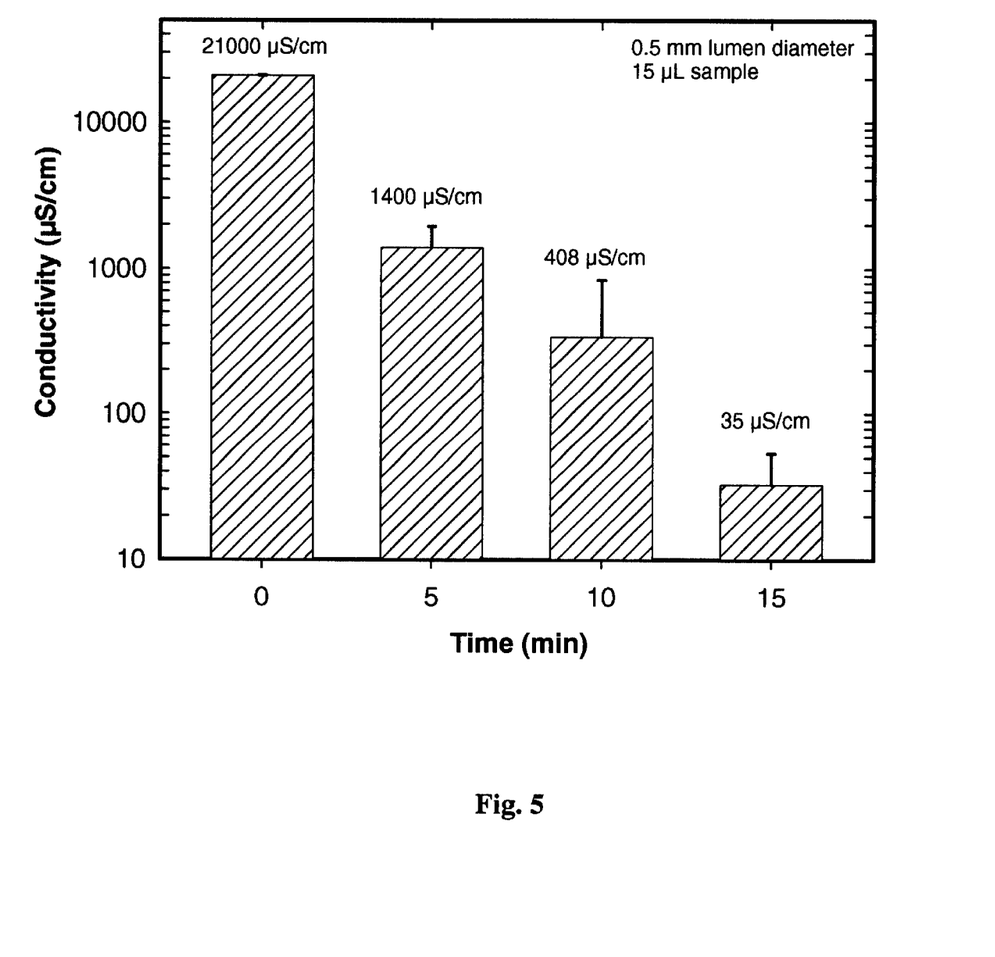
FIG. 5 is a bar chart showing reduction in conductivity of a test solution versus time. The values for 5, 10, and 15 minutes are 1430, 408, and 35 $\mu$S/cm respectively.
Figure 6:
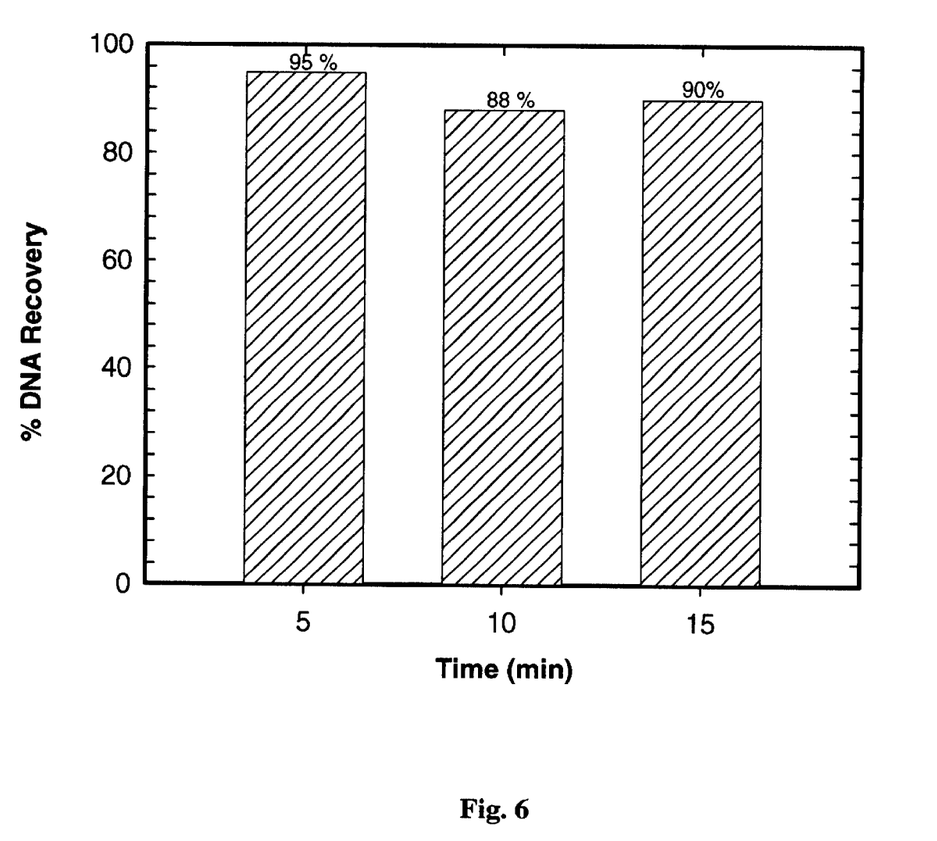
FIG. 6 is a bar chart showing retention of nucleic acid at each time interval of the experiment shown in FIG. 4. In this experiment, the desalting was performed passively and the buffer in the resin chamber was recirculated.
Figure 7:
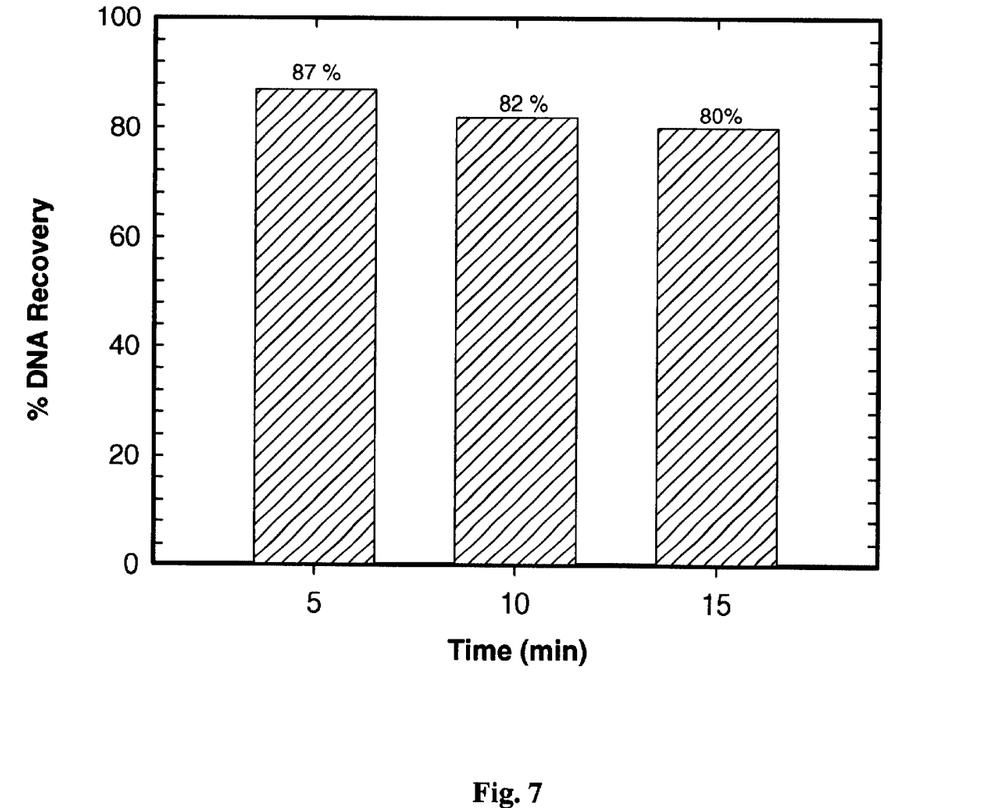
FIG. 7 is a bar chart showing retention of nucleic acid at time intervals 5, 10, and 15 minutes of the experiment shown in FIG. 5. The percentage of nucleic acid retention at these time intervals is 87%, 82%, and 80% respectively.
Figure 8:
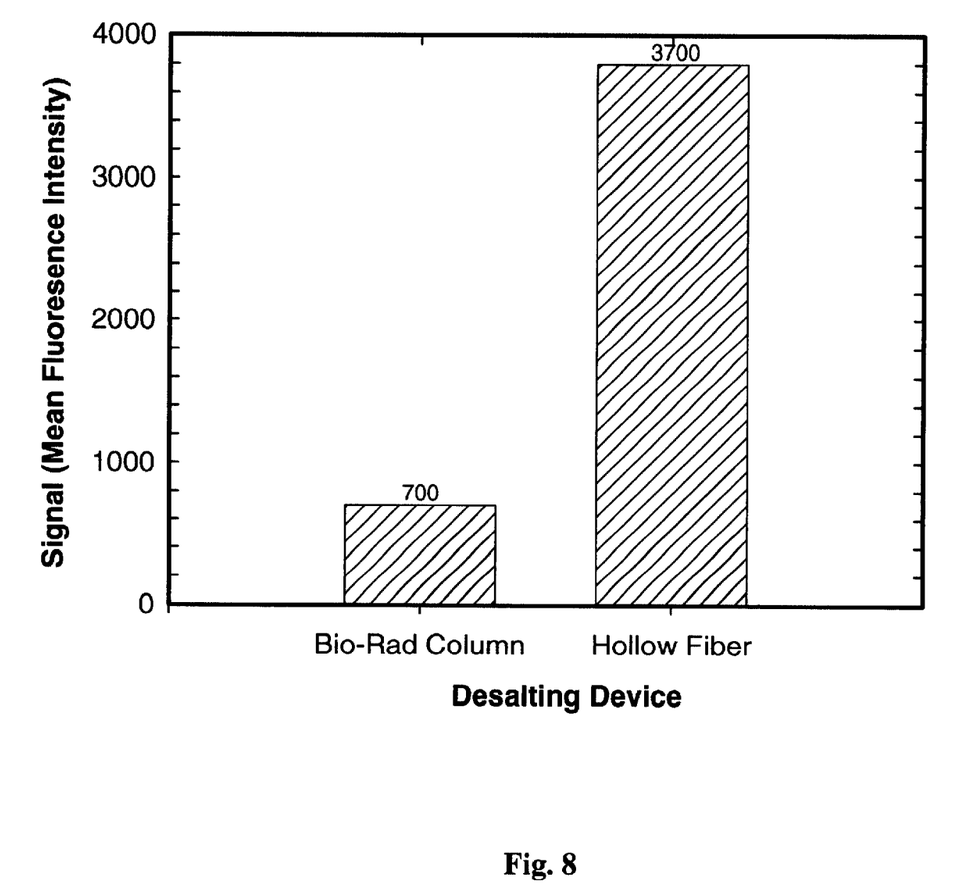
FIG. 8 is a bar chart showing the hybridization signal of the same SDA target desalted on a Biorad spin column versus the hollow fiber/ion-exchange device.

A biological sample comprising a nucleic acid amplification reaction that had undergone strand displacement amplification was desalted using an apparatus of the invention (in this example pore cut off=10 kDa (A/G Technology, 0.5 mm lumen, 200 mm length), resin=mixed bed (Bio-Rad, AG 501-X8), passive desalting for 15 minutes) and in a separate control using a commercial gel filtration spin column (Bio-Rad). After desalting by passing the sample through either the apparatus or the spin column, the sample was electronically addressed to capture sites on an electronically addressable microarray. The level of amplified nucleic acid captured was determined by the mean fluorescent intensity (MFI) of the captured amplicons after labeling with a fluorescent dye. As shown in FIG. 8, the sample that was desalted using the apparatus of the invention yielded a signal of 3,700 MFI as compared to 700 MFI for the commercial spin column. This result indicates that the 5.5 fold increase in signal was due to the retention of a higher concentration of the amplicon (i.e., minimal loss of sample) as well as a lower conductivity of the desalted solution.

EXAMPLE 2

In this example, a nucleic acid sample containing Factor V specific sequence that had undergone PCR amplification was desalted using either the apparatus of the invention (in this example pore cut off=10 kDa (A/G Technology, 0.5 mm lumen, 200 mm length), resin=mixed bed (Bio-Rad, AG 501-X8), passive desalting for 15 minutes) or a commercial gel-filtration spin column. Following PCR, the PCR primers were removed from the reaction mix using PCR clean up columns (Qiagen). The DNA sample was then processed by the two methods. Results indicated that the sample desalted using the apparatus of the invention yielded 20% more DNA than the sample processed via the spin column (4.5 ng/ul vs. 3.6 ng/ul).

In obtaining this result, the samples were denatured by heating at 95° C. for 5 minutes followed by adjustment of the desalted solution in 50 mM histidine. The samples were then electronically addressed to capture pads of a microarray for hybridization with anchored Factor V specific SDA primers. Conductivity of the desalted solutions was indirectly indicated by measurement of the level of amplicons produced from carrying out anchored SDA wherein hybridization efficiency reflects how well the desalted solutions allowed electronic transfer of the templates to the capture pads. The amplification results show that the hollow fiber/resin combination desalted DNA sample has a similar amplification efficiency to the gel filtration desalted DNA with resulting signal intensities of within 10% for the two procedures.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

We claim:

1. An apparatus for lowering the ionic strength of a low volume solution used in the electronic transport of nucleic acids, proteins, and/or cells comprising: a tubular molecular weight cut-off membrane having a lumen, ion exchange resin, and a chamber surrounding and housing said membrane and resin wherein said membrane has an entrance and an exit port leading through said chamber, said membrane further embedded in and amongst said resin, and said chamber having entrance and exit ports for exchanging a flowable material into and out of said chamber.

2. An apparatus according to claim 1 wherein said lumen of said tubular membrane has a diameter of between 100 $\mu$m and 3 mm.

3. An apparatus according to claim 1 wherein said tubular membrane has a molecular weight cut-off of between 1 kDa and 500 kDa.

4. An apparatus according to claim 1 wherein said tubular membrane is embedded among said resin as a linear tube.

5. An apparatus according to claim 1 wherein said tubular membrane is embedded among said resin in the form of a coil or spiral.

6. An apparatus according to claim 1 wherein said resin is selected from the group consisting of cation exchange resin, anion exchange resin, resin containing a buffer molecule, resin containing histidine, a granular exchange resin, and a powder exchange resin.

7. An apparatus according to claim 1 wherein said membrane further comprises electrodes for measuring conductivity of a solution passing along the lumen of said membrane.

8. An apparatus for lowering the ionic strength of a low volume solution used in the electronic transport of nucleic acids, proteins, and/or cells comprising: a tubular molecular weight cut-off membrane having a lumen, ion exchange resin, electrodialysis electrodes, and a chamber surrounding and housing said membrane, electrodialysis electrodes, and resin wherein said membrane has an entrance and an exit port leading through said chamber, said membrane further embedded in and amongst said resin, said chamber having entrance and exit ports for exchanging a flowable material into and out of said chamber, and said electrodes are positioned in a spaced axial alignment and on opposing sides of said chamber with respect to said membrane.

9. An apparatus according to claim 8 wherein said lumen of said tubular membrane has a diameter of between 100 $\mu$m and 3 mm.

10. An apparatus according to claim 8 wherein said tubular membrane has a molecular weight cut-off of between 1 kDa and 500 kDa.

11. An apparatus according to claim 8 wherein said tubular membrane is embedded among said resin as a linear tube.

12. An apparatus according to claim 8 wherein said tubular membrane is embedded among said resin in the form of a coil or spiral with a resin bed volume of between 0.05 $\mu$l and 10 ml.

13. An apparatus according to claim 8 wherein said resin is selected from the group consisting of cation exchange resin, anion exchange resin, resin containing a buffer molecule, resin containing histidine, a granular exchange resin, and a powder exchange resin.

14. An apparatus according to claim 8 wherein said membrane further comprises electrodes for measuring conductivity of a solution passing along the lumen of said membrane.

15. An apparatus according to claim 8 wherein said electrodialysis electrodes provide either a direct current or an alternating current.

16. An apparatus according to claim 15 wherein said direct current has a value of between 2 and 10 volts.

17. An apparatus according to claim 15 wherein said alternating current has an ampimeric flux of between 0.1 mA/cm$^2$ and 100 mA/cm$^2$ and a frequency of between 0.01 and 0.5 Hz.

18. A Method of lowering the ionic strength of a low volume solution comprising:

a. passing said solution into an apparatus of claim 1 or claim 8; and b. allowing said solution of (a) to remain in said chamber of claim 1 or 8 for between 3 and 15 minutes;

wherein in the case where said solution is passed into an apparatus of claim 8, applying a current across said electrodialysis electrodes while said solution remains in said chamber; and c. retrieving said solution.

* * * * *